(12) United States Patent
Yoshimoto et al.

(10) Patent No.: US 7,435,466 B2
(45) Date of Patent: Oct. 14, 2008

(54) POLYTETRAFLUOROETHYLENE-BASED-RESIN TUBE AND PRODUCTION METHOD THEREOF

(75) Inventors: Hiroyuki Yoshimoto, Settsu (JP); Yasuhiko Sawada, Settsu (JP); Shunji Kasai, Settsu (JP); Shuji Tagashira, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 202 days.

(21) Appl. No.: 10/830,394

(22) Filed: Apr. 23, 2004

(65) Prior Publication Data
US 2004/0213936 A1   Oct. 28, 2004

(30) Foreign Application Priority Data
Apr. 24, 2003 (JP) ............................. 2003-120597
Oct. 9, 2003 (JP) ............................. 2003-350871

(51) Int. Cl.
*B29D 22/00* (2006.01)
*B32B 1/08* (2006.01)

(52) U.S. Cl. .................................................. 428/36.9
(58) Field of Classification Search ................. 428/36.9
See application file for complete search history.

(56) References Cited

U.S. PATENT DOCUMENTS 5,529,820 A * 6/1996 Nomi et al. ................ 428/36.4

FOREIGN PATENT DOCUMENTS

| JP | 8-168521 | 7/1996 |
| JP | 2000-51365 | 2/2000 |
| JP | 2000-316977 | 11/2000 |

* cited by examiner

*Primary Examiner*—Patricia L Nordmeyer
(74) *Attorney, Agent, or Firm*—Sughrue Mion, PLLC

(57) ABSTRACT

It is an object of the present invention to provide a polytetrafluoroethylene-based-resin tube high in longitudinal tensile strength and a method of producing the same.

The present invention provides a polytetrafluoroethylene-based-resin tube characterized in that the tensile strength thereof in the longitudinal direction is not lower than 60 MPa.

7 Claims, 3 Drawing Sheets

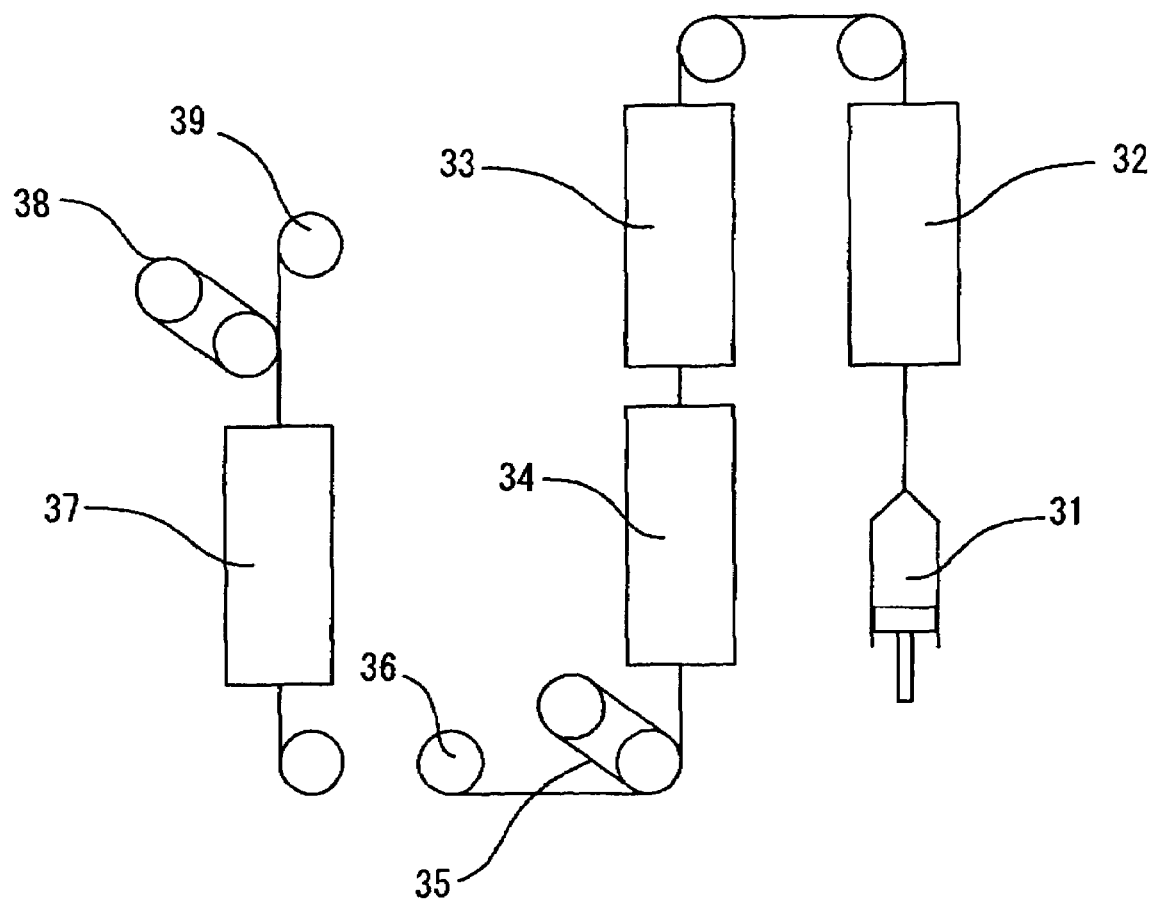
Fig: 3

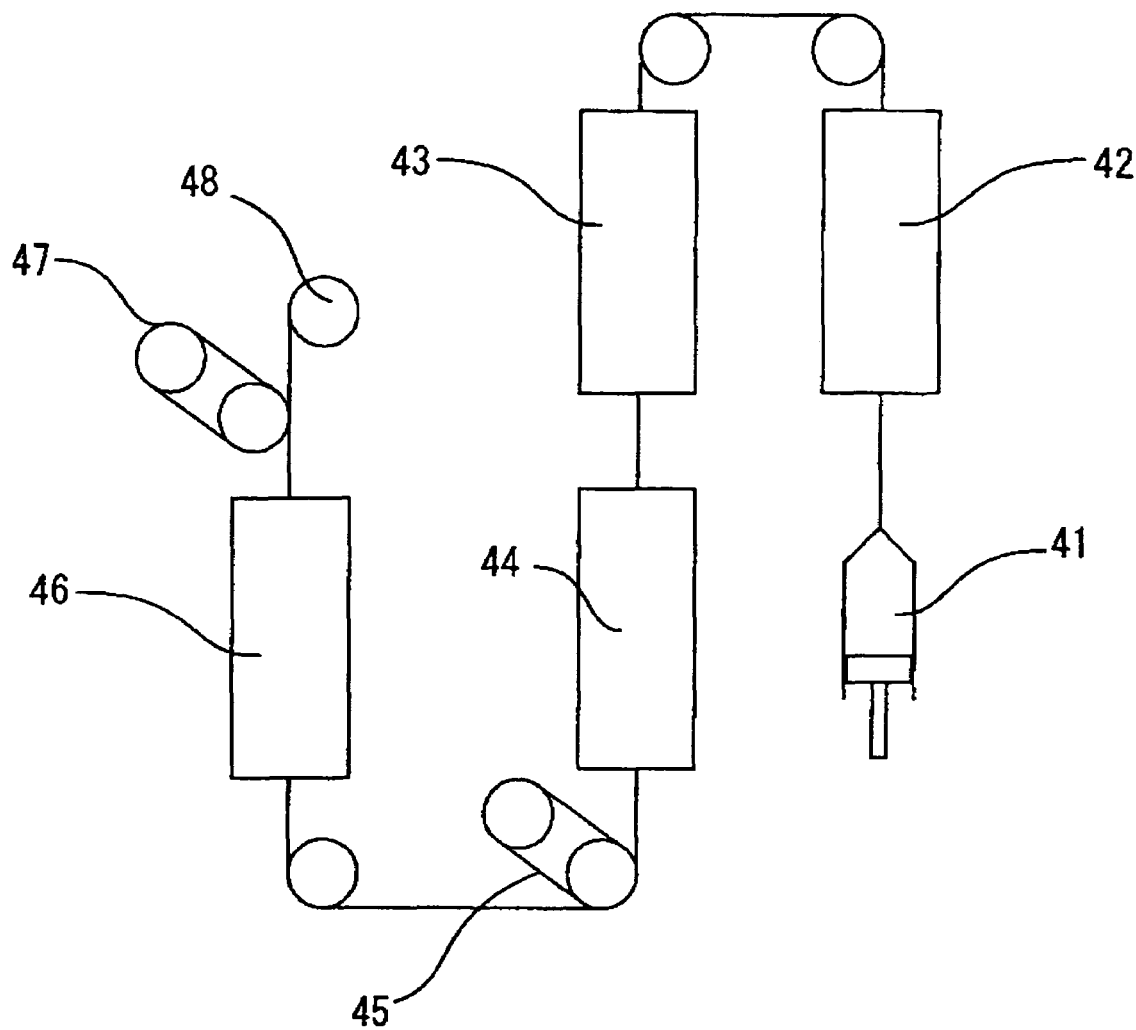
Fig: 4

POLYTETRAFLUOROETHYLENE-BASED-RESIN TUBE AND PRODUCTION METHOD THEREOF

BACKGROUND OF THE INVENTION

1. Field of the Invention

The present invention relates to a polytetrafluoroethylene-based-resin tube and a method of producing the same.

2. Description of the Prior Art

Tubes made of a fluororesin are preferred from the lubricity and chemical resistance viewpoint, in particular. In certain fields of application, such tubes are required to have a thin wall.

Those fluororesin-made thin-wall tubes which are disclosed in JP Kokai (Laid-open Japanese Patent Application) H08-168521, for instance, are the products obtained by molding, by the melt extrusion technique, a mixture composed of a tetrafluoroethylene/perfluoro(alkyl vinyl ether) copolymer and 5-25% by weight of polytetrafluoroethylene [PTFE].

In molding PTFE, which shows a very high melt viscosity, into tubes, it is thinkable to employ the paste extrusion molding technique in lieu of the melt extrusion molding technique. However, the paste extrusion molding technique has a problem in that the wall thickness can be reduced only to a limited extent by that technique.

ASTM D 3295-90, which is concerned with PTFE-made tubes, describes such tubes with an inside diameter of 0.25 mm and a wall thickness of 0.1 mm as ones having the smallest circumference and thinnest wall thickness. However, in some fields of application where extremely thin tubes are required, there is a problem, namely the reduction in wall thickness is still unsatisfactory.

Those thin-wall PTFE tubes which are obtainable by applying a PTFE dispersion onto a core wire, such as a copper wire, sintering the same and, after the formation of an outer resin layer, drawing out the core wire have been proposed (cf. e.g. JP Kokai 2000-316977 and JP Kokai 2000-51365). However, they have a problem, namely they are low in tensile strength.

PTFE-made tubes are desired to be improved in the tensile strength in the longitudinal direction. In particular when they have a thin wall, the tensile strength in the longitudinal direction generally tends to be inferior.

In view of the above-discussed state of the art, it is an object of the present invention to provide a polytetrafluoroethylene-based-resin tube high in longitudinal tensile strength and a method of producing the same.

SUMMARY OF THE INVENTION

The present invention provides a polytetrafluoroethylene-based-resin tube characterized in that the tensile strength thereof in the longitudinal direction is not lower than 60 MPa.

The invention also provides a method of producing polytetrafluoroethylene-based-resin tubes by subjecting original tubes made of a polytetrafluoroethylene-based resin to stretching treatment which method is characterized in that the polytetrafluoroethylene-based-resin-made original tubes are baked ones and the stretching treatment is carried out at 130-327° C.

BRIEF DESCRIPTION OF THE DRAWINGS

FIG. 3 is a schematic illustration, in section, of a mode of practice in which the original PTFE-based-resin tube is once wound up prior to stretching treatment.

FIG. 4 is a schematic illustration, in section, of a process for continuous operation of the baking step through the stretching treatment step.

EXPLANATION OF NUMERICALS

Figure 1:
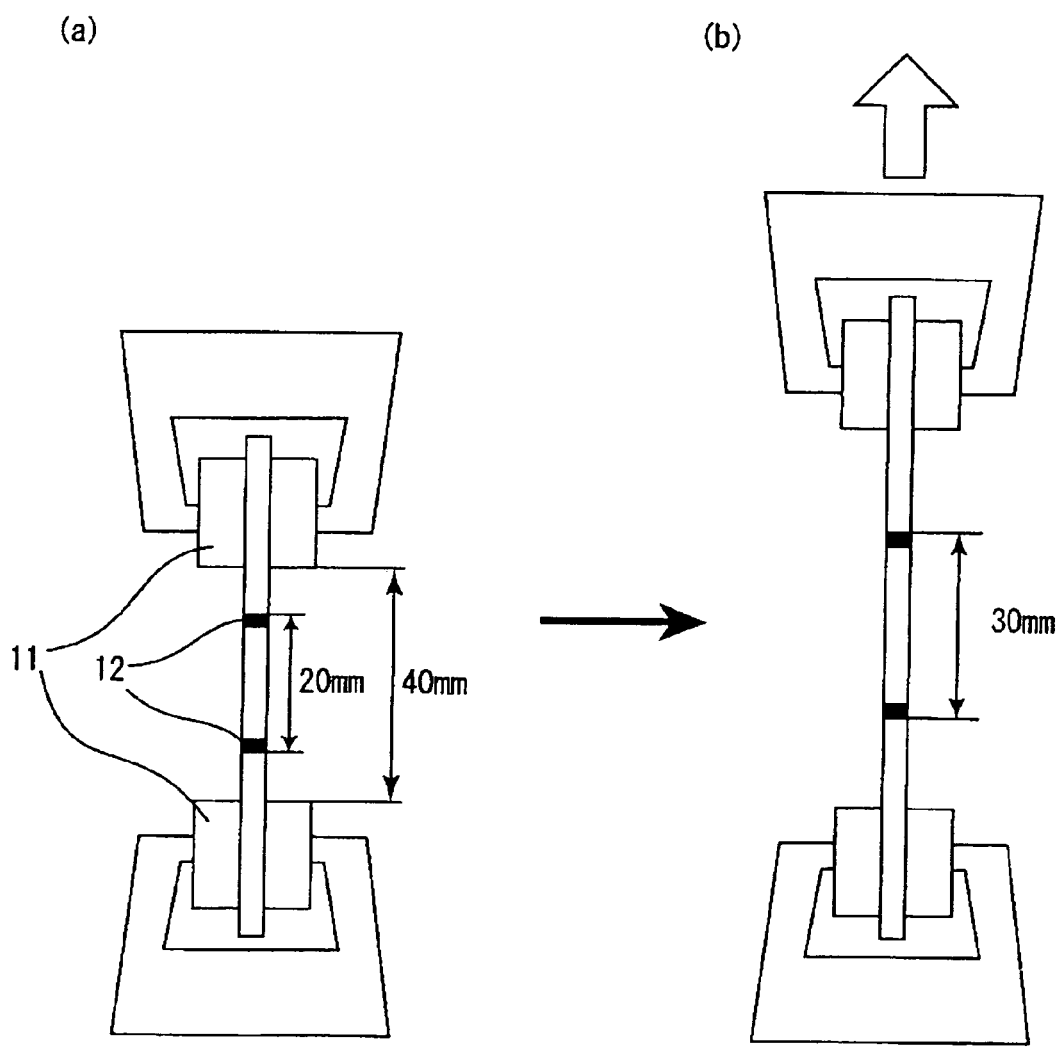
FIG. 1 is a schematic illustration of the tensile test to be carried out. Thus, FIG. 1 (a) is a schematic illustration of the state before stretching, and FIG. 1 (b) is a schematic illustration of the state when the elongation is 50%.

11 chuck
12 marker
21 feeder
22,24 speed adjusting mechanism
25,36,39,48 wind-up machine
23,37,46 stretching oven
32,42 first drying oven
33,43 second drying oven
34,44 molding oven
31,41 extrusion molding machine
35,45 first speed adjusting mechanism
38,47 second speed adjusting mechanism

DETAILED DESCRIPTION OF THE INVENTION

In the following, the invention is described in detail.

In the case of the polytetrafluoroethylene-based-resin tube (hereinafter referred to as "PTFE-based-resin tube") of the invention, the longitudinal tensile strength is not lower than 60 MPa. The longitudinal tensile strength may be not lower than 65 MPa or, further, not lower than 75 MPa. Preferably, it can amount to not less than 70 MPa, more preferably not less than 80 MPa, still more preferably not less than 90 MPa, most preferably not less than 100 MPa. If the tensile strength in the longitudinal direction is within the above range, the upper limit thereto may preferably be set at 800 MPa, more preferably at 600 MPa, still more preferably at 420 MPa. The PTFE-based-resin tube of the invention can be obtained as one whose tensile strength in the longitudinal direction is so high that it falls within the above range; hence it can be adequately used as a long tube required to be high in longitudinal strength.

In this specification, the term "longitudinal direction" refers to the direction perpendicular to the section whose area is minimal among the imaginary sections resulting from imaginary cutting, in section, of the PTFE-based polymer tube in question into two pieces.

In this specification, the tensile strength in the longitudinal direction is the value obtained by measurement at room temperature in accordance with ASTM D 638-00.

The term "room temperature" as used herein refers to a temperature of 20-25° C.

The PTFE-based-resin tube of the invention can be obtained as one showing an elongation at rupture of not more than 50% as measured at room temperature at a pulling rate of 200 mm/minute. The elongation at rupture is preferably not more than 30% and, if it is within the above range, a preferred lower limit may be 2%.

The elongation at rupture can be calculated as follows: Elongation at rupture (%)=100×[(Distance between markers at rupture)−(distance between markers before stretching)]/(distance between markers before stretching). Thus, both ends, as seen in the longitudinal direction, of the tube specimen are placed and fixed in two respective chucks 11 separated by 40 mm, as schematically shown in FIG. 1 (a), the tube specimen is provided with two markers 12 separated by 20 mm, and the tube specimen is stretched in the longitudinal direction, as schematically shown in FIG. 1 (b). FIG. 1 (b) schematically shows, in an example of longitudinal tube specimen stretching, the state after stretching of the tube specimen in the longitudinal direction by 10 cm, namely the state after an increase in distance between markers 12 from 20 cm before stretching to 30 cm.

The PTFE-based-resin tube of the invention preferably has a wall thickness of not thicker than 1 mm. A more preferred upper limit to the wall thickness is 0.8 mm, and a still more preferred upper limit is 0.7 mm. If the wall thickness is within the above range, the lower limit thereto may be set at 0.01 mm. The PTFE-based-resin tube of the invention can be obtained as one having a thin wall thickness such as within the above range, so that it may have a relatively large inside diameter even in those fields of application where tubes of narrow diameter are demanded, for instance, with the result that the reduction in tube contents flow rate and/or the increase in fluid resistance can be suppressed.

The "wall thickness" so referred to herein means the value obtained by crushing the tube in the direction perpendicular to the longitudinal direction, measuring the total thickness using a micrometer and dividing the measured value by 2.

The PTFE-based-resin tube of the invention can have an outside diameter of 0.1 to 10 mm depending on the outside diameter of the intended use thereof and on the original polytetrafluoroethylene-based-resin tube, which is to be described later herein. A preferred lower limit thereto is 0.2 mm, and a preferred upper limit is 6 mm and a more preferred upper limit is 0.6 mm.

The above PTFE-based-resin tube is a tube manufactured from a polytetrafluoroethylene-based resin (hereinafter, "PTFE-based resin"). The PTFE-based resin is a resin consisting of a tetrafluoroethylene homopolymer species [TFE homopolymer] and/or a modified polytetrafluoroethylene species [modified PTFE].

The "TFE homopolymer species and/or modified PTFE species" so referred to herein means a TFE homopolymer free of any modified PTFE, a modified PTFE free of any TFE homopolymer, or a mixture of both a TFE homopolymer and a modified PTFE.

The TFE homopolymer is a polymer of tetrafluoroethylene [TFE] alone.

The modified PTFE is a polymer of TFE and a small proportion of other comonomers. The modified PTFE differs from the TFE homopolymer in that the TFE homopolymer is a homopolymer of TFE as obtained by polymerizing TFE alone, hence it does not contain any other comonomer.

"Polytetrafluoroethylene [PTFE]" is sometimes construed as a term generally denoting a TFE homopolymer. In this specification, however, the "PTFE" appearing in the term "PTFE-based resin" is used not to denote a TFE homopolymer alone but as a mere part of the term "PTFE-based resin", as is evident from the fact that the "PTFE-based resin" can mean not only a TFE homopolymer but also a resin comprising a modified PTFE, as described above.

The other comonomer in the modified PTFE is not particularly restricted but may be any of those copolymerizable with TFE, including, among others, perfluoroolefins such as hexafluoropropene [HFP]; chlorofluoroolefins such as chlorotrifluoroethylene [CTFE]; hydrogen-containing fluoroolefins such as trifluoroethylene; and perfluorinated vinyl ethers.

The perfluorinated vinyl ether is not particularly restricted but may be, for example, a perfluorinated unsaturated compound represented by the general formula (1):

$$CF_2=CF-ORf \tag{1}$$

wherein Rf represents a perfluorinated organic group. The term "perfluorinated organic group" as used herein means an organic group resulting from substitution of fluorine atoms for all the hydrogen atoms bound to carbon atoms. The perfluorinated organic group may contain one or more ether-form oxygen atoms.

The perfluorinated vinyl ether is, for example, a perfluoro (alkyl vinyl ether) [PAVE] of the above general formula (1) in which Rf represents a perfluoroalkyl group containing 1 to 10 carbon atoms, The number of carbon atoms in the perfluoroalkyl group is preferably 1 to 6.

As the perfluoroalkyl group in the above PAVE, there may be mentioned, for example, perfluoromethyl, perfluoroethyl, perfluoropropyl, perfluorobutyl, perfluoropentyl, and perfluorohexyl. Preferred among them is perfluoropropyl.

As the perfluorinated vinyl ether, there may also be mentioned, among others, perfluorinated alkoxyalkyl vinyl ethers and perfluorinated alkylpolyoxyalkylene vinyl ethers represented by the general formula (1) in which Rf is a perfluoro (alkoxyalkyl) group containing 4 to 9 carbon atoms or an organic group represented by the formula:

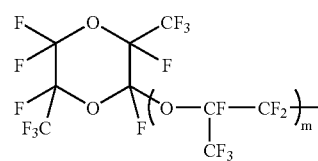

Formula 1 wherein m represents an integer of 0 to 4, or an organic group represented by the formula:

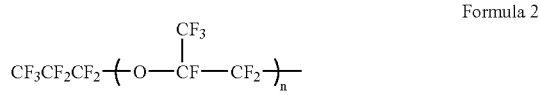

Formula 2 wherein n represents an integer of 1 to 4.

As for the proportion (in % by mass) of the other comonomer in the modified PTFE, the other comonomer is preferably used in such a small amount that it will not provide the resulting modified PTFE with melt fluidity and, for example, when such a perfluorinated vinyl ether as mentioned above is used as the other comonomer, a proportion of not higher than 1% by mass is preferred and a proportion of 0.001 to 1% by mass is more preferred, although the comonomer proportion may vary depending on the other comonomer species employed. When it is less than 0.001% by mass, the creep resistance (total deformation) will be low in some instances. When it exceeds 1% by mass, the mechanical strength features, typically tensile strength, tend to be low and, in the case of using a perfluorinated vinyl ether, which is expensive, any further improvement in creep resistance proportional to the additional content thereof will not be attained; this is economically disadvantageous in certain instances.

The modified PTFE may comprise one single species or two or more species differing in number-average molecular weight and/or copolymerization composition, for instance, and the TFE homopolymer may comprise one single species or two or more species differing in number-average molecular weight.

The TFE homopolymer and modified PTFE mentioned above each preferably has a number-average molecular weight of 1,000,000 to 10,000,000. When the number-average molecular weight is in the above range, the PTFE-based resin tubes obtained will show good physical properties, including mechanical strength characteristics. A more preferred lower limit is 4,000,000, and a more preferred upper limit is 8,000,000.

The TFE homopolymer and modified PTFE mentioned above each preferably is one obtained by emulsion polymerization. The TFE homopolymer and/or modified PTFE powder as obtained by emulsion polymerization is hereinafter sometimes referred to also as "fine powder".

The above-mentioned PTFE-based resin may be a granulation product. The method of granulation may be any of the methods known in the art.

The PTFE-based-resin tube of the invention is preferably produced by subjecting an original tube made of a polytetrafluoroethylene-based resin (hereinafter, "original PTFE-based-resin tube") to stretching treatment. The original PTFE-based-resin tube is a baked one, and the stretching treatment is carried out at 130-327° C. For producing the above-mentioned PTFE-based-resin tube, the method of producing PTFE-based-resin tubes according to the invention can be utilized.

The PTFE-based-resin tube of the invention is one subjected to stretching treatment and, therefore, can have a high level of tensile strength in the longitudinal direction. Furthermore, it retains its original extensibility only to a slight extent, so that it has good dimension stability. Whether a tube has been subjected to stretching treatment or not can be generally known according to whether the tube shrinks, or not, in the direction of stretching upon cooling following heating to a temperature not lower than the melting point thereof.

The PTFE-based-resin tube of the invention, which is the product of subjecting an original PTFE-based-resin tube, which is to be described later herein, to stretching treatment, has no porosity and can be appropriately used in those fields of application in which the tube contents are a fluid, while the fluid is prevented from oozing out.

The method of producing PTFE-based-resin tubes according to the invention comprises subjecting original PTFE-based-resin tubes to stretching treatment to give the desired PTFE-based-resin tubes. The original PTFE-based-resin tubes are baked ones, and the stretching treatment is carried out at 130-327° C.

In this specification, the "original PTFE-based-resin-tube" means a tubular body obtained by tube forming using the PTFE-based resin mentioned above and capable of giving the PTFE-based-resin tube of the invention when subjected to stretching treatment. The original PTFE-based-resin tube is a baked one.

In the above-mentioned tube forming, the paste extrusion technique is preferably employed, and the paste extrusion technique may be any of those known in the art.

The tubular molding obtained by the above method of tube forming is baked in a baking oven. The tubular molding is, for example, an extruded tube as extruded from a paste extruder.

The tubular body as the original PTFE-based-resin tube may also be a wrapping tube obtained by baking a tubular molding resulting from wrapping a PTFE-based-resin tape extruded from a paste extruder, with or without baking, around a core material, and removing the core material.

The tubular molding is baked generally by heating the same at a temperature not lower than the primary melting point of the PTFE-based resin, generally at around 400° C. When the tubular molding is under heating at above the primary melting point, it is low in fluidity and retains its tubular form but is in a state very weak in tensile strength. Therefore, it is preferred that no strong tensile load be applied to the tubular molding.

The primary melting point is the melting point of the PTFE-based resin never melted before.

After baking in a baking oven, the above tubular molding is cooled until a specific temperature is reached, to give an original PTFE-based-resin tube. The specific temperature is not particularly restricted but may be a temperature lower than the temperature at which the PTFE-based resin once melted begins to crystallize (namely, the secondary melting point of the PTFE-based resin). A temperature not higher than 300° C. is preferred, however, since the crystallization of PTFE-based resins generally takes place until they are cooled to about 300° C. In cases where cooling is carried out in air at room temperature, room temperature may be employed as the specific temperature. In this specification, the above specific temperature is sometimes referred to as "cooling temperature".

In this specification, the "tubular molding", such as the one resulting from wrapping a PTFE-based-resin tape around a core material, as mentioned above, or the extruded tube mentioned above, includes, within the meaning thereof, those tubular moldings resulting from wrapping of a tape obtained by the paste extrusion technique around a core material or directly resulting from tube molding by the paste extrusion technique that have been baked in the manner mentioned above but have not yet arrived at the cooling temperature defined above. Thus, the term "tubular molding" as used in this specification refers to the one in the above-mentioned step of baking and, after completion of the baking step, to the one at a temperature exceeding the cooling temperature defined above.

The above-mentioned original PTFE-based-resin tube is the one cooled until arrival of the tubular molding at the cooling temperature defined above and is the tube prior to completion of the stretching treatment for obtaining the PTFE-based-resin tube of the invention.

The method of producing PTFE-based-resin tubes according to the invention makes it possible to stretch the original PTFE-based-resin tube in its tubular form without rendering it porous by subjecting, to stretching treatment, the original PTFE-based-resin tube resulting from tube molding, baking and the subsequent cooling to a temperature below the secondary melting point of the PTFE-based resin, as described above. If no baking step is carried out before stretching, the tube tends to become porous upon stretching treatment. If the stretching treatment is carried out while maintaining a temperature above the secondary melting point of the PTFE-based resin following baking, the tube is in a state of decreased melt viscosity and decreased tensile strength, hence it is susceptible to breakage.

The original PTFE-based-resin tube preferably has an outside diameter of 1 to 10 mm, although the outside diameter may be varied according to the intended use of the final product. When it exceeds 10 mm, no efficient stretching can be accomplished any longer in some instances. A more preferred lower limit to the outside diameter of the PTFE-based-resin tube is 1.05 mm, and a more preferred upper limit thereto is 5 mm.

The original PTFE-based-resin tube preferably has a wall thickness of 0.1 to 3 mm, although the wall thickness may be varied according to the intended use of the final product. When the wall thickness is less than 0.1 mm, it becomes necessary to reduce the bore diameter of the paste extruder die and/or increase the core pin outside diameter, with the result that cracking or porosity may be encountered in certain instances. When it exceeds 3 mm, the wall thickness reduction by stretching treatment tends to be insufficient. A more preferred lower limit to the wall thickness of the original PTFE-based-resin tube is 0.3 mm, and a more preferred upper limit thereto is 2 mm.

As for the section of the original PTFE-based-resin tube, which is perpendicular to the longitudinal direction, the outer and inner circumferences thereof may be circular, or the outer and/or inner circumference may be noncircular, namely the tube in question may be the so-called deformed tube. The deformed tube is not particularly restricted but may be, for example, one having two or more round or rectangular holes in its section perpendicular to the longitudinal direction thereof.

The original PTFE-based-resin tube will be kept in shape even after longitudinal stretching treatment.

The method of producing PTFE-based-resin tubes according to the invention consists in subjecting the above-mentioned original PTFE-based-resin tube to stretching treatment. By carrying out the stretching treatment, it becomes possible to obtain PTFE-based-resin tubes thin in wall thickness and high in longitudinal tensile strength.

In this specification, the above-mentioned "stretching treatment" does not include, in its general concept, any procedure showing a stretching effect in the process from tube molding, such as paste extrusion, through preparation of the original PTFE-based-resin tube via baking. Thus, the stretching treatment does not include the procedure of winding up the original PTFE-based-resin tube by means of a wind-up apparatus 36, shown in the schematic sectional view in FIG. 3, which may cause extension of the original tube.

The stretching procedure for carrying out the above stretching treatment is not particularly restricted but may be any of those procedures by which the original PTFE-based-resin tube can be stretched in the longitudinal direction. It may be a mechanical or manual stretching procedure. From the industrial viewpoint, mechanical stretching is preferred, and the degree of mechanical stretching can be finely adjusted, for example, by means of a speed control system. From the temperature adjustment viewpoint, the stretching procedure for the above stretching treatment is preferably carried out in a drafting or stretching oven.

In the above stretching procedure, the speed ratio for stretching is preferably 1.5 to 20, although it depends, among others, on the reduction ratio [R.R.] of the paste extruder or some other extrusion molding machine and on the degree of stretching of the tubular molding in the process of producing the original PTFE-based-resin tube, if such stretching is effected in that process.

Figure 2:
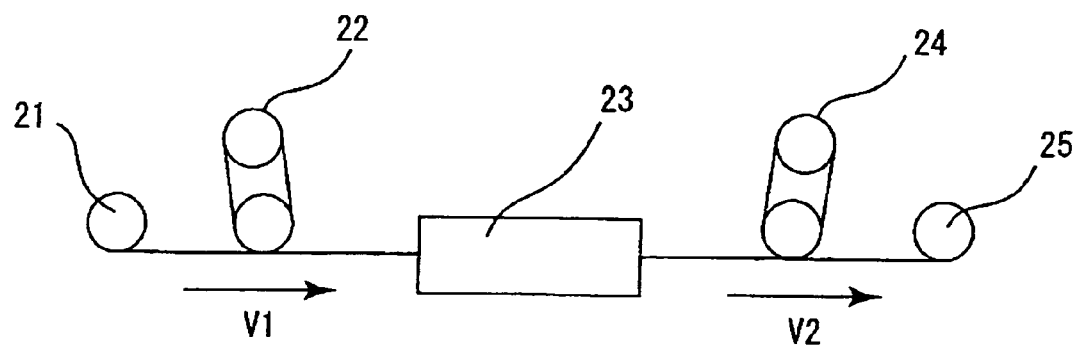
FIG. 2 is a schematic illustration, in section, of a method of stretch speed ratio adjustment through speed controller adjustment.

In this specification, the "stretching speed ratio" is the ratio [V2/V1], where V1 is the tube speed on the speed controller 22 disposed before the stretching oven 23, as schematically shown in section in FIG. 2, and the tube speed V2 on the speed controller 24 disposed behind the stretching oven 23.

A more preferred upper limit to the above stretching speed ratio is 7, and a more preferred lower limit thereto is 2. When the stretching speed ratio is increased within the above preferred range, the resulting PTFE-based-resin tube tends to become increased in tensile strength, thinner in wall thickness and smaller in diameter.

The stretching speed ratio can be adjusted within the above range by means of a speed adjustment system, which is to be mentioned later herein, or a substitute therefor.

The above stretching treatment is carried out at 130-327° C.

If the stretching treatment is carried out at a temperature below 130° C., the original tube will be hardly deformed, possibly resulting in failure in stretching thereof depending on the method of stretching and, as the stretching speed ratio is increased from 1, breakage may occur at about 1.5. At temperatures above 327° C., the tube will melt and lose strength, hence will be readily broken.

When, in the practice of the invention, the stretching treatment is carried out at a temperature not lower than the glass transition point but not higher than the secondary melting point of the PTFE-based resin, it becomes possible to obtain nonporous and thin-wall PTFE-based resin tubes. Generally, the PTFE-based resin mentioned above has a glass transition point of around 130° C. and a secondary melting point of about 327° C., although they may vary depending on the method of determination and/or the copolymer composition in the case of a modified PTFE species.

When the temperature exceeds the glass transition point, the elastic modulus of the amorphous phase rapidly decreases and, therefore, the original tube can be readily deformed and it becomes easy to carry out the stretching treatment at a high stretching speed ratio as compared with the case where the stretching temperature is below the glass transition point.

Further, the stretching treatment is preferably carried out so that the ratio of the outside diameter of the resulting PTFE-based-resin tube to the outside diameter of the original PTFE-based-resin tube may amount to 0.7 or less. On condition that the above ratio is not more than 0.7, a preferred lower limit thereto may be set at 0.1, for instance.

The above stretching treatment may comprise a plurality of repetitions of the stretching procedure. The longitudinal tensile strength of the PTFE-based-resin tube can be improved by repeating that procedure a plurality of times.

The apparatus and placement thereof for carrying out the stretching treatment are not particularly restricted. For example, there may be mentioned a flowchart schematically shown, in section, in FIG. 2, according to which a feeder 21 is loaded with the original PTFE-based-resin tube, which is then fed to a speed adjusting mechanism 22, passed through a stretching oven 23, then sent to a speed adjusting mechanism 24 and wound up by a wind-up machine 25. On that occasion, the feeder 21 is equipped with a feed resisting mechanism to develop a certain level of torque so that the original tube may be inhibited from slipping on the speed adjusting mechanism 22.

Typical as each of the two speed adjusting mechanisms, which are intended for adjusting the rate of flow of the original PTFE-based-resin tube, is one in which at least one pair of pulleys provided with a plurality of grooves are used so that the original PTFE-based-resin tube and/or stretched PTFE-based-resin tube may not run free. Either of the speed adjusting mechanisms may be replaced with an unwinding resistance generator, torque motor, wind-up machine or the like.

In carrying out the method of producing PTFE-based-resin tubes according to the invention, the original PTFE-based-resin tube after baking may be once wound up by means of a wind-up machine 36 prior to stretching treatment, as schematically shown, in section, in FIG. 3, or may be continuously subjected to stretching treatment without winding up after baking, as schematically shown, in section, in FIG. 4.

The mode of practice schematically shown, in section, in FIG. 3 in which the original PTFE-based-resin tube is once wound up is preferably employed in those cases where the stretching speed ratio is to be increased, as described later herein. This is because, in the mode in which the steps of baking to stretching are carried out continuously without winding up the original tube once, the tube is at a temperature exceeding the melting point in the baking oven, hence weak in tensile strength and can be readily broken when the tensile force resulting from stretching treatment is transferred to the tubular molding in the baking oven.

In the mode in which the steps of molding to stretching treatment schematically shown, in section, in FIG. 4 are carried out continuously, it is desirable for the reason mentioned above that a first speed adjusting mechanism 45 be disposed between the baking oven 44 and stretching oven 46 to prevent the tubular molding from being broken as a result of transfer of the wind-up tensile force from the wind-up machine 48 to the tubular molding passing through the baking oven 44.

By using the method of producing polytetrafluoroethylene-based-resin tubes according to the invention, it becomes possible to readily obtain thin-wall PTFE-based-resin tubes high in longitudinal tensile strength. The method of producing PTFE-based-resin tubes according to the invention differs from the method comprising subjecting short-length tubes prepared in advance to blow stretching in a mold, for instance, and can increase the longitudinal tensile strength required of long-length tubes, among others, and, furthermore, makes it possible to adjust the degree of stretching in the longitudinal direction, which has been difficult to adjust in the art as a result of appearance of differences therein from site to site, through adjustment of the stretching speed ratio.

It is also possible to use two or more pieces of the PTFE-based-resin tube of the invention in bundle.

The PTFE-based-resin tube of the invention may be provided, according to the intended use thereof, with an external resin layer as a polyamide or polyurethane layer or further with a braid layer between the PTFE-based-resin tube and the resin layer just mentioned above.

The field of application of the PTFE-based-resin tube of the invention is not particularly restricted but the tube can be used, for example, as a fuel transport tube such as a jet plane fuel transport tube or a rocket fuel transport tube; a high-temperature corrosive fluid transport tube to be used in chemical or nuclear plants; a tube for transporting fluids to be free from contamination, for example foodstuffs and chemicals; a steam hose; a tube for transporting tacky substances; a brake hose to be used in hydraulic controllers; an electric insulating tube such as an insulating cover tube for electronic apparatus or devices or a wire-covering tube; a tube for medical use; or a heat exchanger tube. The tube is preferably used as a tube for medical use owing to its good biocompatibility and, when its transparency and good visibility are taken into consideration, it is preferably used as a fluid transport tube, a tube for medical use or the like.

The polytetrafluoroethylene-based-resin tube of the invention is preferably one intended for use as a fuel transport tube, fluid transport tube, brake hose, electric insulating tube, tube for medical use, or heat exchanger tube.

The fuel transport tube, fluid transport tube, brake hose, electric insulating tube, tube for medical use, or heat exchanger tube which consists of the PTFE-based-resin tube of the invention also constitutes an aspect of the present invention.

The polytetrafluoroethylene-based-resin tube of the invention, which has the constitution described hereinabove, can be obtained as a thin-wall one high in longitudinal tensile strength, and the method of producing polytetrafluoroethylene-based-resin tubes according to the invention, which has the constitution described hereinabove, makes it possible to readily obtain the above-mentioned polytetrafluoroethylene-based-resin tube.

BEST MODE FOR CARRYING OUT THE INVENTION

The following examples illustrate the present invention in further detail. These examples are, however, by no means limitative of the scope of the invention.

EXAMPLE 1

An extrusion auxiliary (18 parts by mass; trademark: Isopar G, product of Exxon Chemical) was added to 100 parts by mass of a PTFE fine powder (trademark: Polyflon PTFE F-210, product of Daikin Industries), and the mixture was allowed to stand in a polyethylene bottle for 24 hours for maturation. Thorough mixing was then effected by 5 minutes of agitation using a tumbler shaker.

Lumps of the PTFE fine powder were removed using a #8 sieve, and the undersize fraction was subjected to tubular molding preparation by the paste extrusion technique. Thus, primary preforming was carried out by compressing the fraction under a pressure of 5 MPa for 15 minutes. To fill the gap between the primary preform and the cylinder, the primary preform obtained was inserted into the cylinder of an extrusion molding machine 31, the head was closed, and secondary preforming was carried out by applying a pressure of 20 MPa for 1 minute.

The cylinder inside diameter of the extrusion molding machine 31 was 38 mm, the mandrel outside diameter 16 mm, the core pin outside diameter 1.06 mm and the die inside diameter 1.27 mm, and the die temperature was set at 60° C.

Then, the tubular molding extruded from the extrusion molding machine 31 at a ram velocity of 10 m/minute was passed through a first 3-meter-long drying oven 32 set at 130° C., a second 3-meter-long drying oven 33 set at 190° C. and a baking oven 34 set at 440° C. and then wound up by a wind-up machine 36 at a rate of 20 m/minute, as schematically shown, in section, in FIG. 3, to give an original PTFE-based-resin tube A with an outside diameter of 1.06 mm and an inside diameter of 0.8 mm. Its tensile strength was 28 MPa. During baking, speed adjustment was carried out using a first speed adjusting mechanism 35 so that any excessive tensile force might not be applied to the tubular molding.

The original PTFE-based-resin tube A once wound up was fed to a stretching oven 37 having a total length of 6 m and set at 320° C. at a speed of 4 m/minute. The tube discharged from the stretching oven 37 was drawn by a wind-up machine 39 at a rate of 20 m/minute to give a PTFE-based-resin tube with an outside diameter of 0.5 mm and a wall thickness of 0.05 mm.

The tensile strength of the thus-obtained PTFE-based-resin tube was measured and found to be 190 MPa.

EXAMPLE 2

An original PTFE-based-resin tube A was prepared in the same manner as in Example 1. After departure from the corresponding baking oven 44, as schematically shown, in section, in FIG. 4, it was once cooled to a temperature not exceeding 300° C. and then sent to a first speed adjusting mechanism 45. The first speed adjusting mechanism 45 was composed of three pairs of pulleys, and the speed of the original PTFE-based-resin tube A was adjusted to 20 m/minute so that the tube A might be prevented from slipping. After departure from the first speed adjusting mechanism 45, the original PTFE-based-resin tube A was fed to a stretching oven 46 having a total length of 6 m and maintained at 320° C., then to a second speed adjusting mechanism 47, and wound up by a wind-up machine 48 at a rate of 100 m/minute to give a PTFE-based-resin tube with an outside diameter of 0.5 mm and a wall thickness of 0.045 mm.

The tensile strength of the thus-obtained PTFE-based-resin tube was measured and found to be 196 MPa.

COMPARATIVE EXAMPLE 1

The steps of auxiliary admixing, preforming, paste extrusion, drying and baking were carried out in the same manner as in Example 1, and the speed of the wind-up machine 36 schematically shown, in section, in FIG. 3 was set at 35 m/minute. The tube was broken in the baking oven 34.

COMPARATIVE EXAMPLE 2

The procedure of Example 2 was followed in the same manner except that the temperature of the stretching oven 46 schematically shown, in section, in FIG. 4 was set at 100° C. After departure from the baking oven 44, the tube was drawn by means of the wind-up machine 48 at a speed of 40 m/minute. The tube was broken in the stretching oven 46.

COMPARATIVE EXAMPLE 3

A copper wire with a diameter of 0.5 mm was immersed in an aqueous dispersion (trademark: Polyflon PTFE D-1, product of Daikin Industries), followed by drying and baking. This procedure was repeated five times in total to form a 20-μm-thick PTFE film on the copper wire. Then, the copper wire was drawn out to give a tube with a diameter of 0.55 mm and a wall thickness of 20 μm. The tensile strength of the thus-obtained tube was measured at room temperature and found to be 10 MPa.

EXAMPLES 3 TO 7 AND COMPARATIVE EXAMPLES 4 TO 6

Tubes and PTFE-based-resin tubes 1 to 5 were produced in the same manner as in Example 1 except that stretching was carried out by varying the stretching speed ratio so that the outside diameters of the resulting tubes and PTFE-based-resin tubes might have the values shown in Table 1. The tubes produced were subjected to tensile strength measurement at room temperature. The tensile strength measurement was carried out at a pulling rate of 100 m/minute. The area of the section perpendicular to the longitudinal direction of each test specimen was calculated using each of the tubes and PTFE-based-resin tubes 1 to 5 before tensile strength testing.

The results obtained in the above manner are shown in Table 1.

EXAMPLES 8 AND 9

An original PTFE-based-resin tube B (outside diameter: 10.5 mm; wall thickness: 1.0 mm; tensile strength: 44.9 MPa) was obtained in the same manner as in Example 1 except that Polyflon PTFE F-104 (product of Daikin Industries) was used as the PTFE fine powder species, the extrusion molding machine 31 had an inside diameter of 90 mm, the mandrel had an outside diameter of 20 mm, the core pin had an outside diameter of 8.5 mm, the die had an inside diameter of 10.5 mm, and the die temperature was set at 60° C.

The original PTFE-based-resin tube B obtained was stretched while varying the stretching speed ratio so that the outside diameter of the resulting PTFE-based-resin tube might amount to either of the values indicated in Table 2. The thus-produced PTFE-based-resin tubes were subjected to tensile strength measurement at room temperature.

EXAMPLE 10

An original PTFE-based-resin tube C (outside diameter: 10.0 mm; wall thickness: 1.0 mm; tensile strength: 35.0 MPa) was obtained in the same manner as in Examples 8 and 9 except that Polyflon PTFE F-201 (product of Daikin Industries) was used as the PTFE fine powder species.

The original PTFE-based-resin tube C obtained was stretched while varying the stretching speed ratio so that the outside diameter of the resulting PTFE-based-resin tube might amount to the value indicated in Table 2. The thus-produced PTFE-based-resin tube was subjected to tensile strength measurement at room temperature.

The thus-obtained results are shown in Table 2.

TABLE 1

|  |  | Outside diameter (mm) | Wall thickness (mm) | Tensile strength (MPa) |
|---|---|---|---|---|
| Original PTFE-based-resin (Polyflon F-201) tube A | | 1.06 | 0.130 | 28 |
| Example 3 | PTFE-based-resin tube 1 | 0.6 | 0.067 | 114 |
| Example 4 | PTFE-based-resin tube 2 | 0.5 | 0.049 | 234 |
| Example 5 | PTFE-based-resin tube 3 | 0.45 | 0.03 | 412 |
| Example 6 | PTFE-based-resin tube 4 | 0.30 | 0.024 | 592 |
| Example 7 | PTFE-besed-resin tube 5 | 0.7 | 0.085 | 76 |
| Comparative Example 4 | Tube 1 | 0.9 | 0.119 | 26 |
| Comparative Example 5 | Tube 2 | 0.8 | 0.112 | 35 |
| Comparative Example 6 | Tube 3 | 0.75 | 0.104 | 36 |

TABLE 2

|  |  | Outside diameter (mm) | Wall thickness (mm) | Tensile strength (MPa) |
|---|---|---|---|---|
| Original PTFE-based-resin (Polyflon F-104) tube B | | 10.5 | 1.0 | 44.9 |
| Example 8 | PTFE-based-resin tube 6 | 5.5 | 0.62 | 71.9 |
| Example 9 | PTFE-based-resin tube 7 | 5.0 | 0.51 | 109.3 |
| Original PTFE-based-resin (Polyflon F-201) tube C | | 10.0 | 1.0 | 35.0 |
| Example 10 | PTFE-based-resin tube 8 | 4.5 | 0.51 | 74.3 |

From the data shown in Table 1 and Table 2, it was found that the tensile strength increases as the wall thickness increases.

EXAMPLE 9

The original PTFE-based-resin tube A was prepared in the same manner as in Example 1.

This original PTFE-based-resin tube A was once wound up and then fed to the stretching oven 37 shown in FIG. 3 as maintained at 135° C. at a speed of 4 m/minute, and wound up by means of the wind-up machine 39 at a rate of 10 m/minute to give a PTFE-based-resin tube with an outside diameter of 0.685 mm and a wall thickness of 0.076 mm.

The tensile strength of the thus-obtained PTFE-based-resin tube was measured and found to be 65 MPa.

COMPARATIVE EXAMPLE 7

A tube with an outside diameter of 0.8 mm and a wall thickness of 0.153 mm was produced in the same manner in Example 4 except that the stretching oven temperature was set at 110° C. and the wind-up machine 39 was operated at a wind-up speed of 8 m/minute. The tensile strength of the thus-obtained tube was measured and found to be 35 MPa. The speed of the wind-up machine 39 was further increased and, when it arrived at 9.6 m/minute, the tube was broken.

The tube of the invention can be used as a tube for medical use or as a heat exchanger tube, among others.

The invention claimed is:

1. A polytetrafluoroethylene-based-resin tube characterized in that the tensile strength thereof in the longitudinal direction is not lower than 60 MPa, said polytetrafluoroethylene-based-resin tube consists of polytetrafluoroethylene and/or modified polytetrafluoroethylene, which tube is nonporous and produced by subjecting an original polytetrafluoroethylene-based-resin tube to stretching treatment, and said original polytetrafluoroethylene-based-resin tube is a baked one.

2. The polytetrafluoroethylene-based-resin tube as set forth in claim 1 which has a wall thickness of not more than 0.08 mm.

3. The polytetrafluoroethylene-based-resin tube as set forth in claim 1, wherein the stretching treatment is carried out at a temperature of 130-327° C.

4. The polytetrafluoroethylene-based-resin tube as set forth in claim 1 which is intended for use as a fuel transport tube, fluid transport tube, brake hose, electrical insulating tube, tube for medical use, or heat exchanger tube.

5. The polytetrafluoroethylene-based-resin tube as set forth in claim 1, wherein the polytetrafluoroethylene-based-resin tube consists of polytetrafluoroethylene homopolymer.

6. A method of producing a polytetrafluoroethylene-based-resin tube characterized in that the tensile strength thereof in the longitudinal direction is not lower than 60 MPa, said polytetrafluoroethylene-based-resin tube consists of polytetrafluoroethylene and/or modified polytetrafluoroethylene, which tube is nonporous and produced by subjecting an original polytetrafluoroethylene-based-resin tube to stretching treatment, and said original polytetrafluoroethylene-based-resin tube is a baked one, said method comprises subjecting said original polytetrafluoroethylene-based-resin tube to stretching treatment at a temperature of 130-327° C.

7. The method as set forth in claim 6, wherein said polytetrafluoroethylene-based-resin tube consist of polytetrafluoroethylene homopolymer.

* * * * *